United States Patent
Choi (10) Patent No.: US 10,441,358 B2
(45) Date of Patent: Oct. 15, 2019

(54) MULTI-FUNCTION LASER IRRADIATING APPARATUS

(71) Applicant: LAMEDITECH CO., LTD., Seoul (KR)

(72) Inventor: Jong Seok Choi, Incheon (KR)

(73) Assignee: Lameditech Co., Ltd., Seoul (KR)

(*) Notice: Subject to any disclaimer, the term of this patent is extended or adjusted under 35 U.S.C. 154(b) by 354 days.

(21) Appl. No.: 15/300,548

(22) PCT Filed: Mar. 17, 2015

(86) PCT No.: PCT/KR2015/002584
§ 371 (c)(1),
(2) Date: Sep. 29, 2016

(87) PCT Pub. No.: WO2015/152539
PCT Pub. Date: Oct. 8, 2015

(65) Prior Publication Data
US 2017/0128131 A1 May 11, 2017

(30) Foreign Application Priority Data
Mar. 31, 2014 (KR) .................. 10-2014-0038078

(51) Int. Cl.
*A61B 18/20* (2006.01)
*A61B 90/00* (2016.01)
*A61B 18/00* (2006.01)

(52) U.S. Cl.
CPC .... *A61B 18/203* (2013.01); *A61B 2018/0047* (2013.01); *A61B 2018/2035* (2013.01); *A61B 2018/2055* (2013.01); *A61B 2090/065* (2016.02)

(58) Field of Classification Search
None
See application file for complete search history.

(56) References Cited

U.S. PATENT DOCUMENTS

2006/0195076 A1* 8/2006 Blumenkranz ..... A61F 9/00736
606/4
2006/0217695 A1* 9/2006 DeBenedictis ...... A61B 18/201
606/18
(Continued)

FOREIGN PATENT DOCUMENTS

| JP | 60-149020 | 8/1985 |
| JP | 60-147008 | 9/1985 |
| JP | 06-051205 | 2/1994 |

(Continued)

OTHER PUBLICATIONS

Int'l. Search Report of PCT/KR2015/002584 dated Jun. 10, 2015.

*Primary Examiner* — Carl H Layno
*Assistant Examiner* — Dacheng Xie
(74) *Attorney, Agent, or Firm* — Greer Burns & Crain, Ltd.

(57) ABSTRACT

The present disclosure relates to a laser irradiating apparatus including a laser resonator configured to generate a laser beam and output the laser beam forwards, a first passage part located in front of the laser resonator and configured to allow the laser beam generated from the laser resonator to pass through, and a second passage part located as being spaced from the first passage part and configured to allow the laser beam passing through the first passage part to pass through.

9 Claims, 4 Drawing Sheets

(56) References Cited

U.S. PATENT DOCUMENTS

2015/0157979 A1\* 6/2015 Park ................. C01B 3/105
423/231
2015/0306418 A1\* 10/2015 Lee .................. A61N 5/0616
607/89

FOREIGN PATENT DOCUMENTS

| JP | 07-265448 | 10/1995 |
| JP | 2003-126276 | 5/2003 |
| JP | 2008-086435 | 4/2008 |
| JP | 2009513189 A | 4/2009 |
| JP | 2010501246 A | 1/2010 |
| JP | 2012-521808 A | 9/2012 |
| JP | 2013-103228 | 5/2013 |
| KR | 10-2007-0044621 A | 4/2007 |
| KR | 10-2008-0056034 | 6/2008 |

\* cited by examiner

MULTI-FUNCTION LASER IRRADIATING APPARATUS

TECHNICAL FIELD

The present disclosure relates to a multi-function laser irradiating apparatus.

BACKGROUND

Recently, as various medical devices have been developed along with the development of various high technologies, high-tech laser devices are being used more often than ever before in the medical field to treat various diseases.

One of the uses of a medical laser is to perforate skin by irradiating a laser to the skin in order to collect blood from the perforated skin, administer drug into a perforation, or remove dots or freckles from the skin.

Further, in the field of dentistry, particularly, for the treatment of caries, a laser device enables a non-contact treatment with a higher accuracy unlike a drill necessarily requiring a mechanical contact. Furthermore, the laser device can minimize pain mainly caused by vibration or heat in a mechanical contact and thus more easily achieve a painless treatment. Therefore, in recent years, laser devices have completely or partially substituted for conventional mechanical devices such as drills.

In this regard, Korea Patent Application Publication No. 10-2007-0044621 (entitled "A medical laser irradiator and irradiation method") describes an adapter for supplying power, a main body for generating a laser by controlling an intensity of a laser by the user, and a handpiece for irradiating a laser generated from the main body.

DISCLOSURE OF THE INVENTION

Problems to be Solved by the Invention

The present disclosure is conceived to solve the above-described problem of the conventional technology, and provides a multi-function laser irradiating apparatus capable of adjusting a laser for various purposes.

Means for Solving the Problems

According to a first aspect of the present disclosure, a multi-function laser irradiating apparatus includes: a laser resonator configured to generate a laser beam and output the laser beam forwards; a first passage part located in front of the laser resonator and configured to allow the laser beam generated from the laser resonator to pass through; and a second passage part located in front of the first passage part as being spaced therefrom and configured to allow the laser beam passing through the first passage part to pass through. The first passage part includes at least two first passage units selected from among a first diffusion lens, a first focusing lens, a first wavelength filter part, a first alignment lens, a first multi-focusing lens, and a first through-hole part and is movable in order for the laser beam generated from the laser resonator to be selectively supplied to any one of the at least two first passage units. The second passage part includes at least two second passage units selected from among a second diffusion lens, a second focusing lens, a second wavelength filter part, a second alignment lens, a second multi-focusing lens, a second through-hole part, and a window part and is movable in order for the laser beam generated from the laser resonator to be selectively supplied to any one of the at least two second passage units.

Effects of the Invention

According to the aspect of the present disclosure, a laser beam can be selectively supplied to any one of at least two first passage units and selectively supplied to any one of at least two second passage units. Thus, a laser can be adjusted for various purposes. Therefore, it is possible to eliminate the necessity of having to buy multiple laser irradiating apparatuses.

MODE FOR CARRYING OUT THE INVENTION

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "on" that is used to designate a position of one element with respect to another element includes both a case that the one element is adjacent to the another element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Hereinafter, the present disclosure will be described in detail with reference to the accompanying drawings.

Figure 1:
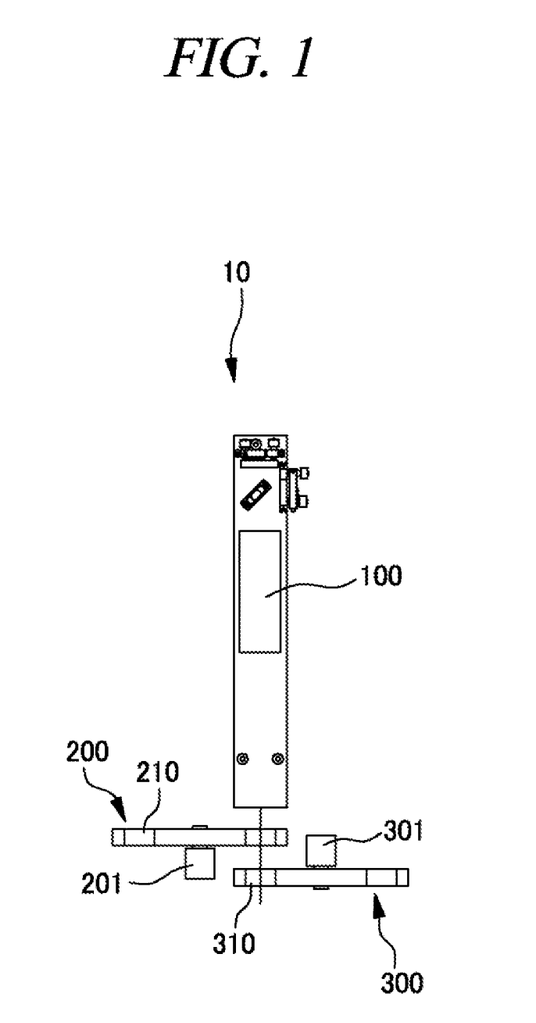
FIG. 1 is a schematic diagram of a multi-function laser irradiating apparatus in accordance with an exemplary embodiment.

Referring to FIG. 1, a multi-function laser irradiating apparatus 10 in accordance with an exemplary embodiment includes a laser resonator 100, a first passage part 200, and a second passage part 300.

The laser resonator 100 is configured to generate a laser beam and output the laser beam forwards.

For example, the laser resonator 100 is supplied with electric energy and amplifies light to generate light energy such as a laser selected from a gas laser, a liquid laser, a solid laser, and a semiconductor laser and outputs the light energy to the outside.

The above-exemplified laser resonator 100 has a generally-used configuration which is obvious to those skilled in the art. Therefore, a detailed explanation thereof will be omitted.

The first passage part 200 is located in front of the laser resonator 100. Further, the first passage part 200 is configured to allow the laser beam generated from the laser resonator 100 to pass through.

Herein, the first passage part 200 is located in front of the laser resonator 100. This may mean that a laser beam output from the laser resonator 100 is directly transferred to the first passage part 200. However, the first passage part 200 is not limited to be located in front of the laser resonator. A transmission medium, such as an optical fiber, an optical aperture, etc., capable of transmitting a laser beam may be further provided between the laser resonator 100 and the first passage part 200, so that the laser beam output from the laser resonator 100 may pass through the above-described transmission medium and then may be irradiated to the first passage part 200.

Further, the first passage part 200 may allow the laser beam output from the laser resonator 100 to primarily pass through, which does not mean that the first passage part 200 is a medium which the laser beam output from the laser resonator 100 first passes through, but means that the laser beam output from the laser resonator 100 primarily passes through the first passage part 200 from among the first passage part 200 and the second passage part 300.

The second passage part 300 is located in front of the first passage part 200 as being spaced therefrom. Further, the second passage part 300 allows the laser beam passing through the first passage part 200 to pass through.

The second passage part 300 is located in front of the first passage part 200 as being spaced therefrom. This may mean that, for example, the second passage part 300 is located as being spaced from the first passage part 200 at a distance suitable for a laser beam to be diffused to a sufficient size if the laser beam is diffused through a first diffusion lens 211 of the first passage part 100 and then irradiated to the second passage part 300.

Further, the second passage part 300 may allow the laser beam output from the laser resonator 100 to secondarily pass through, which means that the laser beam passing through the first passage part 200 is irradiated to the second passage part 300 and then passes through the second passage part 300, but is not limited thereto. The laser beam passing through the first passage part 200 may be bent through reflection, distribution, etc. and then irradiated to the second passage part 300.

Figure 2:
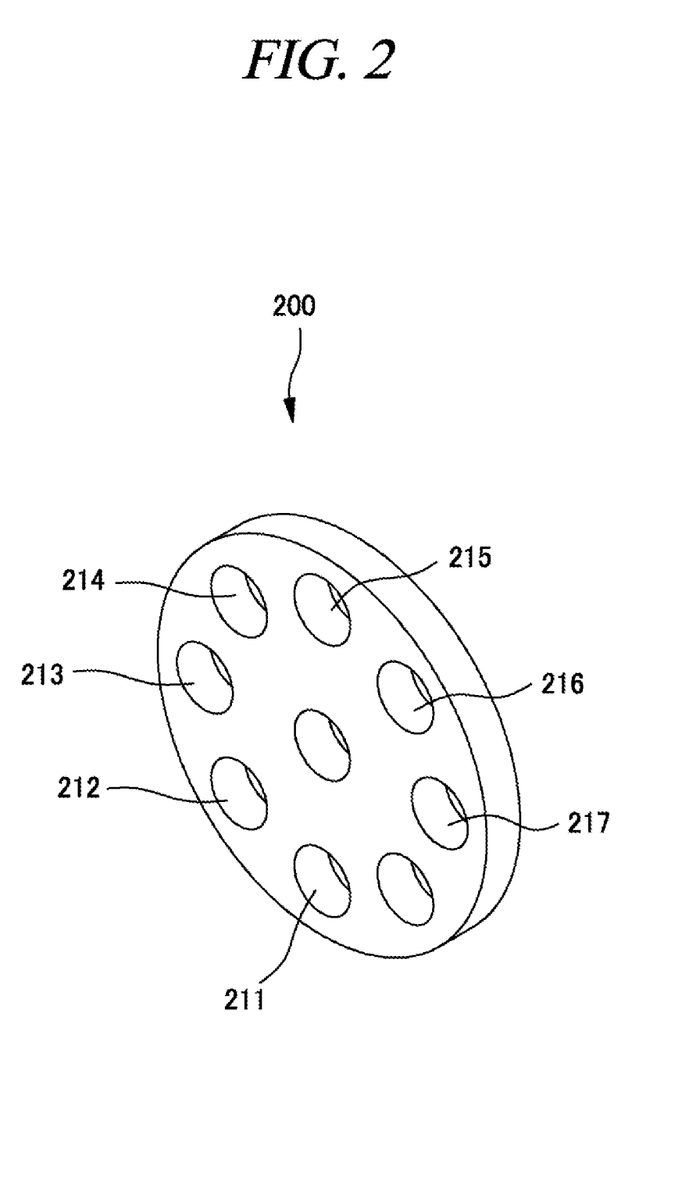
FIG. 2 is a perspective view of a first passage part in accordance with an exemplary embodiment.

The first passage part 200 includes at least two first passage units 210 selected from among the first diffusion lens 211, a first focusing lens 212, a first wavelength filter part 213, a first alignment lens 214, a first multi-focusing lens 215, and a first through-hole part 216 and is movable in order for the laser beam generated from the laser resonator 100 to be selectively supplied to any one of the at least two first passage units 210.

Figure 3:
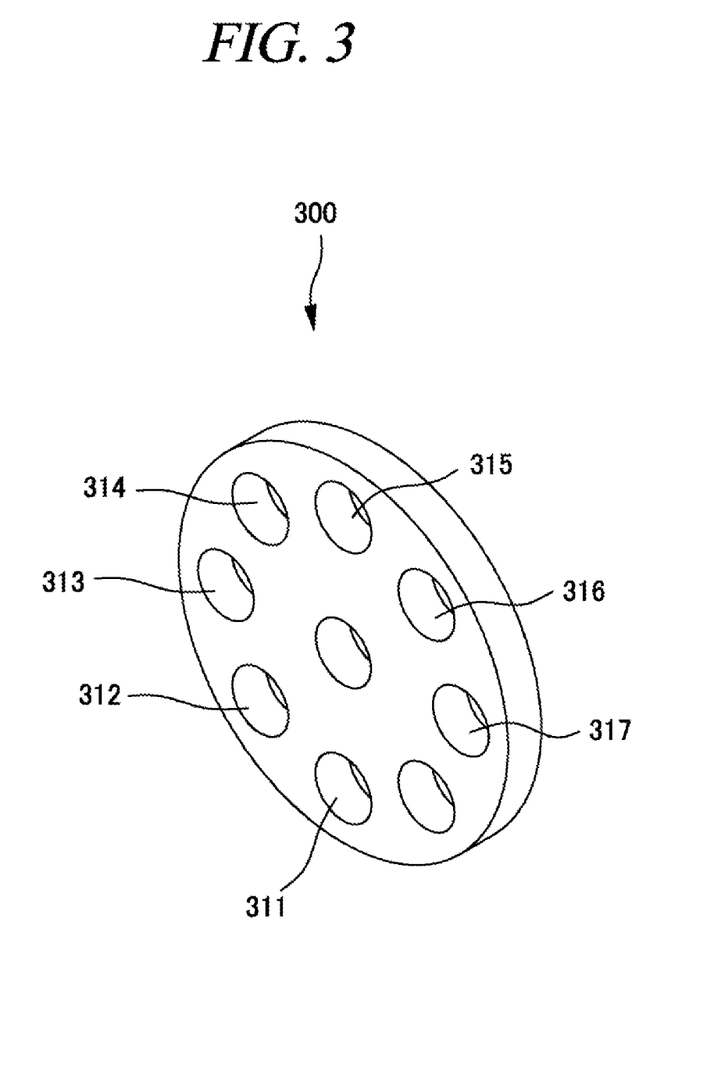
FIG. 3 is a perspective view of a second passage part in accordance with an exemplary embodiment.

The second passage part 300 includes at least two second passage units 310 selected from among a second diffusion lens 311, a second focusing lens 312, a second wavelength filter part 313, a second alignment lens 314, a second multi-focusing lens 315, and a second through-hole part 316 and is movable in order for the laser beam generated from the laser resonator 100 to be selectively supplied to any one of the at least two second passage units 310.

If a user makes an operation input to output a desired laser beam, the first passage unit 210 and the second passage unit 310 may be selected in response to the operation input. Further, the first passage part 200 and the second passage part 300 may be moved in order for a laser beam to be supplied to the selected first passage unit 210 and the second passage unit 310.

For example, if there is made an operation input to irradiate a laser beam for perforating skin to form multiple perforations, the first passage part 200 is moved and the first diffusion lens 211 is selected, and the second passage part 300 is moved and the second multi-focusing lens 315 is selected. Then, a laser beam generated from the laser resonator 100 passes through the first diffusion lens 211 and is uniformly dispersed and irradiated to the second multi-focusing lens 315. Then, the laser beam passes through the multi-focusing lens 315 and is irradiated to the skin focusing on multiple points.

Further, the first through-hole part 216 and the second through-hole part 316 may mean empty spaces which a laser beam directly passes through.

The laser beam output from the laser resonator 100 may pass through the selected first passage unit 210 and the selected second passage unit 310 and then may be changed in properties to be suitable for various purposes.

The first passage part 200 may include the first diffusion lens 211, and the second passage part 300 may include one or more units selected from among the second diffusion lens 311, the second wavelength filter part 313, the second alignment lens 314, and the second multi-focusing lens 315.

For example, the first passage part 200 may include the first diffusion lens 211 and one or more first passage units 210 except the first diffusion lens 211. Further, the second passage part 300 may include one second passage unit 310 selected from among the second diffusion lens 311, the second wavelength filter part 313, the second alignment lens 314, and the second multi-focusing lens 315 and one or more second passage units 310 except the included second passage unit 310.

Hereinafter, there will be described a case where the first diffusion lens 211 of the first passage part 200 is selected and one second passage unit 310 of the second passage part 300 is selected from among the second diffusion lens 311, the second wavelength filter part 313, the second alignment lens 314, and the second multi-focusing lens 315.

The above-described term "selected" may mean that the first passage part 200 and the second passage part 300 are moved, so that the first passage unit 210 and the second passage unit 310 corresponding to an operation input are located on a laser beam path.

The first diffusion lens 211 of the first passage part 200 may be selected, and one of the second diffusion lens 311, the second alignment lens 314, the second multi-focusing lens 315, and the second wavelength filter part 313 of the second passage part 300 may be selected for a purpose of use.

The first diffusion lens 211 of the first passage part 200 may be selected and the second diffusion lens 311 of the second passage part 300 may be selected. In this case, a part of a laser beam incident through the first diffusion lens 211 may be expanded and then incident into the second diffusion lens 311. Then, the part of the laser beam may pass through the second diffusion lens 311 and may be expanded to a large area and irradiated to an irradiation target portion. If the multi-function laser irradiating apparatus 10 is used in a hospital, the irradiation target portion may be the skin of a patient. The first diffusion lens 211 and the second diffusion lens 311 can be usefully used when a weak laser beam is irradiated to a large skin area. The first diffusion lens 211 and the second diffusion lens 311 may be selected and used for treatment for skin improvement such as skin peeling, microablation, removal of freckles and blemishes, and pigmentation.

The first diffusion lens 211 of the first passage part 200 may be selected and the second wavelength filter part 313 of the second passage part 300 may be selected. In this case, a part of a laser beam irradiated through the first diffusion lens 211 may be expanded and then irradiated to the second wavelength filter part 313. Then, the part of the laser beam may pass through the second wavelength filter part 313 and a laser beam having a specific wavelength may be selected and irradiated to an irradiation target portion. The first diffusion lens 211 and the second wavelength filter part 313 can be used in filler plastic surgery for removing hot flushes. Further, multiple second wavelength filter parts 313 may be provided. Each of the second wavelength filter parts 313 is configured to filter a specific wavelength. Thus, a user can select and use multiple specific wavelengths.

The first diffusion lens 211 of the first passage part 200 may be selected and the second alignment lens 314 of the second passage part 300 may be selected. In this case, a part of a laser beam irradiated through the first diffusion lens 211 may be expanded and then incident into the second alignment lens 314. Then, the part of the laser beam may pass through the second alignment lens 314 and irradiated to an irradiation target portion with a uniform wavelength.

The first diffusion lens 211 of the first passage part 200 may be selected and the second multi-focusing lens 315 of the second passage part 300 may be selected. In this case, a part of a laser beam irradiated through the first diffusion lens 211 may be expanded and then irradiated to the second multi-focusing lens 315. Then, the part of the laser beam may pass through the second multi-focusing lens 315 to be multi-focused. The term "multi-focusing" may mean forming multiple perforations in an irradiation target portion by irradiating a laser beam one time. The first diffusion lens 211 and the second multi-focusing lens 315 can be used for acne scars, skin regeneration, perforation for drug injection, scar removal, and the like.

Further, the second passage part 300 may include a window part 317.

The window part 317 may suppress introduction of smoke or foreign substances generated during a treatment into the first passage part 200 and the laser resonator 100.

The first passage part 200 may include one or more units selected from among the first focusing lens 212, the first diffusion lens 211, the first wavelength filter part 213, the first alignment lens 214, and the first multi-focusing lens 215, and the second passage part 300 may include the window part 317.

For example, the first passage part 200 may include one first passage unit 210 selected from among the first diffusion lens 211, the first focusing lens 212, the first wavelength filter part 213, the first alignment lens 214, and the first multi-focusing lens 215 and one or more first passage units 210 except the included first passage unit 210. Further, the second passage part 300 may include the window part 317 and one or more second passage units 310 except the window part 317.

Hereinafter, there will be described a case where one first passage unit 210 of the first passage part 200 is selected from among the first diffusion lens 211, the first focusing lens 212, the first wavelength filter part 213, the first alignment lens 214, and the first multi-focusing lens 215 and the window part 317 of the second passage part 300 is selected.

The first diffusion lens 211 of the first passage part 200 may be selected and the window part 317 of the second passage part 300 may be selected. In this case, a laser beam irradiated from the laser resonator 100 may pass through the first diffusion lens 211 and may be diffused and then irradiated to the window part 317. The diffused laser beam may pass through the window part 317 and then may be irradiated to an irradiation target portion.

The focusing lens 212 of the first passage part 200 may be selected and the window part 317 of the second passage part 300 may be selected. In this case, a laser beam irradiated from the laser resonator 100 may pass through the first focusing lens 212 and may be converged and then irradiated to the window part 317. The converged laser beam may pass through the window part 317 and then may be irradiated to an irradiation target portion. In this case, the laser beam may be focused by the first focusing lens 212 and used for blood collecting, spot removal, tooth grinding, and the like. Further, the window part 317 of the second passage part 300 may be selected to suppress introduction of smoke or foreign substances generated during a treatment into the first passage part 200 and the laser resonator 100.

The first wavelength filter part 213 of the first passage part 200 may be selected and the window part 317 of the second passage part 300 may be selected. In this case, a laser beam irradiated from the laser resonator 100 may pass through the first wavelength filter part 213 and a laser beam having a specific wavelength may be selected and irradiated to the window part 317. The laser beam having a specific wavelength may pass through the window part 317 and then may be irradiated to an irradiation target portion. Further, multiple first wavelength filter parts 213 may be provided. Each of the first wavelength filter parts 213 is configured to filter a specific wavelength. Thus, a user can select and use multiple specific wavelengths.

The first alignment lens 214 of the first passage part 200 may be selected and the window part 317 of the second passage part 300 may be selected. In this case, a laser beam irradiated from the laser resonator 100 may pass through the first alignment lens 214 and may be aligned and then irradiated to the window part 317. The aligned laser beam may pass through the window part 317 and then may be irradiated to an irradiation target portion.

The first multi-focusing lens 215 of the first passage part 200 may be selected and the window part 317 of the second passage part 300 may be selected. In this case, a laser beam irradiated from the laser resonator 100 may pass through the first multi-focusing lens 215 and may be multi-focused and then irradiated to the window part 317. The multi-focused laser beam may pass through the window part 317 and then may be irradiated to an irradiation target portion.

The first passage part 200 can be moved along a predetermined path, and the first passage unit 210 may be located corresponding to the predetermined path.

For example, in the first passage part 200, at least two first passage units 210 may be located as being spaced from each other. Further, as the first passage part 200 is moved, a laser beam irradiated from the laser resonator 100 can be accurately irradiated to one selected first passage unit 210.

Further, if a user makes an operation input to output a desired laser beam, the first passage unit 210 corresponding to the operation input may be selected and the first passage part 200 may be moved in order for the laser beam from the laser resonator 100 to be output to the selected first passage unit 210.

The second passage part 300 can be moved along a predetermined path, and the second passage unit 310 may be located corresponding to the predetermined path.

For example, in the second passage part 300, at least two second passage units 310 may be located as being spaced from each other. Further, as the second passage part 300 is moved, the laser beam passing through the first passage part 200 can be accurately irradiated to one selected second passage unit 310.

Further, if a user makes an operation input to output a desired laser beam, the second passage unit 310 corresponding to the operation input may be selected and the second passage part 300 may be moved in order for the laser beam passing through the first passage unit 210 to be output to the selected second passage unit 310.

The first passage part 200 and the second passage part 300 may be moved manually.

A first motor driving part 201 configured to drive the first passage part 200 and a second motor driving part 301 configured to drive the second passage part 300 may be provided. The first motor driving part 201 may provide the first passage part 200 with driving power for movement, and the second motor driving part 301 may provide the second passage part 300 with driving power for movement.

As the first motor driving part 201 operates, the driving power may be transferred to the first passage part 200. Thus, the first passage part 200 may be moved along a predetermined path. As the second motor driving part 301 operates, the driving power may be transferred to the second passage part 300. Thus, the second passage part 300 may be moved along a predetermined path.

For example, referring to FIG. 2, in the first passage part 200, the first passage units 210 may be located as being spaced from each other around a first shaft parallel to a laser beam output direction. In this case, the above-described predetermined path may be a circular arc path rotating around the first shaft, and the first passage part 200 may be rotated and moved along this rotation path by the first motor driving part 201.

For example, referring to FIG. 3, in the second passage part 300, the second passage units 310 may be located as being spaced from each other around a second shaft parallel to the laser beam output direction. In this case, the above-described predetermined path may be a circular arc path rotating around the second shaft, and the second passage part 300 may be rotated and moved along this rotation path by the second motor driving part 301.

Further, the first shaft and the second shaft may be the same shaft. The first passage part 200 and the second passage part 300 may be connected to one shaft, and each of the first passage part 200 and the second passage part 300 may be rotated and moved by the one shaft.

According to another exemplary embodiment, in the first passage part 200, the first passage units 210 may be located as being spaced from each other on a straight path. In this case, the above-described predetermined path may be a straight path, and the first passage part 200 may be linearly moved along the straight path by the first motor driving part 201. The first motor driving part 201 may move the first passage part 200 such that the first passage unit 210 is located on a laser beam path and a laser beam can be accurately irradiated to the first passage unit 210.

Further, in the second passage part 300, the second passage units 310 may be located as being spaced from each other on a straight path. In this case, the above-described predetermined path may be a straight path, and the second passage part 300 may be linearly moved along the straight path by the second motor driving part 301. The second motor driving part 301 may move the second passage part 300 such that the second passage unit 310 is located on a laser beam path and a laser beam can be accurately irradiated to the second passage unit 310.

A third passage part (not illustrated) may be further provided between the first passage part 200 and the second passage part 300 or in front of the second passage part 300. The third passage part may include at least two third passage units selected from among a third diffusion lens, a third focusing lens, a third wavelength filter part, a third alignment lens, a third multi-focusing lens, a third through-hole part, and a window part and is movable in order for a laser beam generated from the laser resonator 100 to be selectively supplied to any one of the at least two third passage units.

Three passage parts, such as the first passage part 100, the second passage part 200, and the third passage part, that allow a laser beam generated from the laser resonator 100 to pass through may be provided.

For example, the first passage part 100, the second passage part 200, and the third passage part may be provided, and the first diffusion lens 211 of the first passage part 200 may be selected, the second diffusion lens 311 of the second passage part 300 may be selected and the third multi-focusing lens of the third passage part may be selected. In this case, a laser beam irradiated from the laser resonator 100 may pass through the first diffusion lens 211 and then may be diffused. The diffused laser beam may pass through the second diffusion lens 311 and may be further diffused. The further diffused laser beam may pass through the third multi-focusing lens to be multi-focused and may be irradiated to an irradiation target portion.

The multi-function laser irradiating apparatus 10 of the present disclosure may further include a forward and backward driving part configured to move the first passage part 200 and the second passage part 300 forwards and backwards.

By moving the first passage part 200 and the second passage part 300 forwards and backwards, a distance between an irradiation target portion and the first and second passage parts 200 and 300 can be adjusted and a size of a laser beam spot irradiated to the irradiation target portion can be adjusted.

Figure 4:
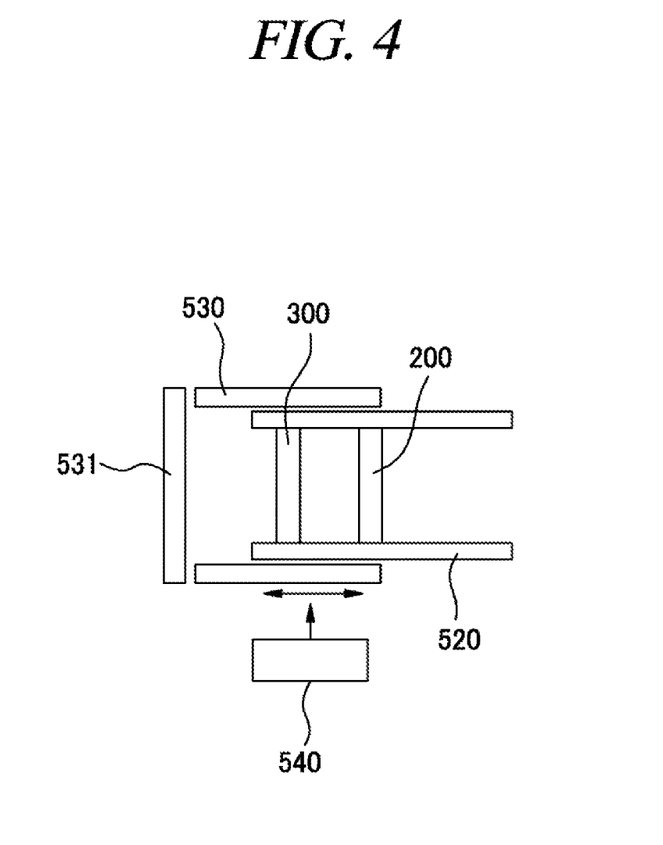
FIG. 4 is a schematic cross-sectional view provided to explain a forward and backward driving part in accordance with an exemplary embodiment.

Referring to FIG. 4, the forward and backward driving part may include a beam barrel 520, a spacer barrel 530, and a forward and backward driving unit 540.

The first passage part 200 and the second passage part 300 may be mounted within the beam barrel 520.

Further, the beam barrel 520 may serve as a passage which a laser beam passing through the first passage part 200 passes through.

The spacer barrel 530 may be inserted to an outer periphery of the beam barrel 520.

The forward and backward driving unit 540 may move the beam barrel 520 forwards and backwards in relation to an irradiation target portion in front thereof.

For example, a front part of the spacer barrel 530 is fixed as being spaced at a predetermined distance or in contact with an irradiation target portion and the beam barrel 520 is moved forwards and backwards, and, thus, a distance between the irradiation target portion and the beam barrel 520 can be adjusted and a size of a laser beam spot irradiated to the front part of the spacer barrel 530 can be adjusted.

Further, although not illustrated in the drawings, the beam barrel 520 further includes the third passage part located between the first passage part 200 and the second passage part 300 or in front of the second passage part 300.

The spacer barrel 530 may include a spacer window part 531 which is replaceably combined with the front part of the spacer barrel 530 and replaced for each patient.

The spacer window part 531 combined with the spacer barrel 530 is replaced for each patient. Thus, it is possible to suppress transmission of infection between patients and also possible to suppress infiltration of smoke, foreign substances, etc. generated during a treatment to the inside.

The multi-function laser irradiating apparatus 10 of the present disclosure may further include a safety means configured to control laser beam generation from the laser resonator 100.

The safety means refers to a device configured to suppress careless irradiation of a laser beam and thus suppress accidents such as loss of sight.

To this end, the safety means may include a grip sensor, a touch sensor, and a slide sensor.

After the safety means including the grip sensor, the touch sensor, and the slide sensor determines whether it is safe, the laser resonator 100 may generate a laser beam.

The grip sensor may be located at a part to be gripped by a user to use the multi-function laser irradiating apparatus 10, and configured to sense the user's grip. For example, in the multi-function laser irradiating apparatus 10, the part to be gripped by the user may be of handpiece type, gun type, or the like.

For example, the grip sensor may include one or more sensors selected from among a light sensor in which a light is blocked by a griping hand of the user, a heat sensor configured to sense heat of the gripping hand, and a pressure sensor configured to sense a gripping pressure.

Further, the multi-function laser irradiating apparatus 10 can accurately irradiate a laser beam to a location to which the user wants to irradiate while being fixed in contact with an irradiation target portion.

The touch sensor may be located at a part to be in contact with the irradiation target portion, and configured to determine a touch on the irradiation target portion. For example, referring to FIG. 4, the touch sensor may be provided on or around the spacer window part 531.

For example, the touch sensor may be a current sensor configured to sense a micro electrical current flowing through the irradiation target portion or a temperature sensor configured to sense a temperature of the irradiation target portion. However, the touch sensor is not limited thereto, and may include various sensors depending on the properties of the irradiation target portion and thus determine a touch on the irradiation target portion.

The slid sensor is configured to sense a pressure applied to the irradiation target portion from a part in contact with the irradiation target portion.

For example, the slid sensor may be a pressure sensor configured to sense a backward slide of a mounting plate on which the spacer barrel and the beam barrel are mounted. For example, referring to FIG. 4, the slide sensor may be provided on or around the spacer window part 531.

When the user brings the multi-function laser irradiating apparatus 10 into contact with the irradiation target portion and applies a pressure thereto, the mounting plate is slid backwards and the pressure is measured by the pressure sensor located in back of the mounting plate. If the pressure measured by the pressure sensor is equal to or higher than a predetermined pressure, the laser resonator 100 generates a laser beam.

The laser beam generation from the laser resonator 100 under the control of the safety means will be described. In the multi-function laser irradiating apparatus 10, the grip sensor senses the user's grip of the part to be gripped by the user, the touch sensor senses that the part to be in contact with the irradiation target portion is in contact with the irradiation target portion, and then, the slide sensor senses a pressure applied to the irradiation target portion from the part in contact with the irradiation target portion. Then, if the pressure is equal to or higher than a predetermined pressure, the laser resonator 100 can be in an active state in which it can generate a laser beam.

In the active state, the laser resonator 100 may immediately generate a laser beam. Otherwise, in the active state, when the user gives a command to generate a laser beam by additional manipulation of a button or the like, the laser resonator 100 may generate a laser beam.

Therefore, in the multi-function laser irradiating apparatus 10 of the present disclosure, a laser beam is selectively supplied to any one of at least two first passage units 210 and selectively supplied to any one of at least two second passage units 310. Thus, a laser can be adjusted for various purposes. Therefore, it is possible to eliminate the necessity of having to buy multiple laser irradiating apparatuses 10.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

[Explanation of Codes]

10: Multi-function laser irradiating apparatus
100: Laser resonator
200: First passage part
201: First motor driving part
210: First passage unit
211: First diffusion lens
212: First focusing lens
213: First wavelength filter part
214: First alignment lens
215: First multi-focusing lens
216: First through-hole part
300: Second passage part
301: Second motor driving part
310: Second passage unit
311: Second diffusion lens
312: Second focusing lens
313: Second wavelength filter part
314: Second alignment lens
315: Second multi-focusing lens
316: Second through-hole part
317: Window part
520: Beam barrel
530: Spacer barrel

[Explanation of Codes]

531: Spacer window part
540: Forward and backward driving unit

I claim:

1. A multi-function laser irradiation apparatus comprising:
a laser resonator configured to generate a laser beam and output the laser beam forward;
a first passage part located in front of the laser resonator and configured to allow the laser beam generated from the laser resonator to pass through;
a second passage part located in front of the first passage part as being spaced therefrom and configured to allow the laser beam passing through the first passage part to pass through,
wherein the first passage part includes at least two first passage units selected from among a first diffusion lens, a first focusing lens, a first wavelength filter part, a first alignment lens, a first multi-focusing lens, and a first through-hole part and is movable in order for the laser beam generated from the laser resonator to be selectively supplied to any one of the at least two first passage units, and
the second passage part includes at least two second passage units selected from among a second diffusion lens, a second focusing lens, a second wavelength filter part, a second alignment lens, a second multi-focusing lens, a second through-hold part, and a window part and is movable in order for the laser beam generated from the laser resonator to be selectively supplied to any one of the at least two second passage units; and
a forward and backward driving part configured to move the first passage part and the second passage part forwards and backwards,
wherein the forward and backward driving part includes:
a beam barrel on which the first passage part and the second passage part are mounted;
a spacer barrel inserted on an outer periphery of the beam barrel; and
a forward and backward driving unit configured to move the beam barrel forwards and backwards in relation to an irradiation target portion in front thereof.

2. The multi-function laser irradiating apparatus of claim 1,
wherein the first passage part includes the first diffusion lens, and
the second passage part includes one or more units selected from among the second diffusion lens, the second alignment lens, the second multi-focusing lens, and the second wavelength filter part.

3. The multi-function laser irradiating apparatus of claim 2, wherein the second passage part includes the window part.

4. The multi-function laser irradiating apparatus of claim 1,
wherein the first passage part includes one or more units selected from among the first diffusion lens, the first focusing lens, the first wavelength filter part, the first alignment lens, and the first multi-focusing lens, and the second passage part includes the window part.

5. The multi-function laser irradiating apparatus of claim 1,
wherein the first and second passage parts are movable along a predetermined path, and
the first and second passage units are located corresponding to the predetermined path.

6. The multi-function laser irradiating apparatus of claim 1, further comprising:
a first motor driving part configured to provide the first passage part with driving power for movement; and
a second motor driving part configured to provide the second passage part with driving power for movement.

7. The multi-function laser irradiating apparatus of claim 1,
wherein in the first passage part, the at least two first passage units are located as being spaced from each other around a first shaft parallel to an output direction of the laser beam and in the second passage part, the at least two second passage units are located as being spaced from each other around a second shaft parallel to the output direction of the laser beam, and
the first passage part is rotated around the first shaft and the second passage part is rotated around the second shaft.

8. The multi-function laser irradiating apparatus of claim 1,
wherein at least two first passage units are located as being spaced from each other on a straight path in the first passage part, and at least two second passage units are located as being spaced from each other on a straight path in the second passage part, and
the first passage part is linearly moved along the straight path and the second passage part is linearly moved along the straight path.

9. The multi-function laser irradiating apparatus of claim 1, further comprising:
safety means configured to control laser beam generation from the laser resonator,
wherein the safety means includes:
a grip sensor configured to sense a user's grip;
a touch sensor configured to sense a touch on an irradiation target portion; and
a slide sensor configured to sense a pressure applied to the irradiation target portion.

* * * * *